(12) United States Patent
Gowans et al.

(10) Patent No.: US 11,090,196 B2
(45) Date of Patent: Aug. 17, 2021

(54) ABSORBENT NEGATIVE PRESSURE WOUND THERAPY DRESSING

(71) Applicant: Smith & Nephew PLC, Watford (GB)

(72) Inventors: John Philip Gowans, Hessle (GB); Stephanie Jane Noble, Brough (GB)

(73) Assignee: Smith & Nephew PLC, Watford (GB)

( * ) Notice: Subject to any disclaimer, the term of this patent is extended or adjusted under 35 U.S.C. 154(b) by 405 days.

(21) Appl. No.: 16/067,530

(22) PCT Filed: Dec. 30, 2016

(86) PCT No.: PCT/IB2016/001959
§ 371 (c)(1),
(2) Date: Jun. 29, 2018

(87) PCT Pub. No.: WO2017/115146
PCT Pub. Date: Jul. 6, 2017

(65) Prior Publication Data
US 2019/0151159 A1    May 23, 2019

Related U.S. Application Data

(60) Provisional application No. 62/273,053, filed on Dec. 30, 2015.

(51) Int. Cl.
*A61M 1/00* (2006.01)
*A61F 13/00* (2006.01)
(Continued)

(52) U.S. Cl.
CPC ........ *A61F 13/0223* (2013.01); *A61F 13/022* (2013.01); *A61F 13/0203* (2013.01); *A61F 13/0206* (2013.01); *A61F 13/0209* (2013.01); *A61F 13/0216* (2013.01); *A61F 13/0253* (2013.01); *A61F 13/0266* (2013.01);
(Continued)

(58) Field of Classification Search
CPC ................ A61F 13/022; A61F 13/0223; A61F 13/0203; A61F 13/0206; A61F 13/0209; A61F 13/0216; A61F 13/0253; A61F 13/0266; A61M 1/0086;
(Continued)

(56) References Cited

U.S. PATENT DOCUMENTS 3,972,328 A    8/1976  Chen
4,029,598 A    6/1977  Neisius et al.
(Continued)

FOREIGN PATENT DOCUMENTS

DE          34 43 101     5/1986
DE    20 2004 017 052    7/2005
(Continued)

OTHER PUBLICATIONS

"Technology Watch", May 1989, in 1 page.
(Continued)

*Primary Examiner* — Benjamin J Klein
(74) *Attorney, Agent, or Firm* — Knobbe, Martens, Olson & Bear, LLP

(57) ABSTRACT

Disclosed herein are several embodiments of a wound treatment apparatus employing glue on the backing layer of a wound dressing. In some embodiments, the glue limits saturation of an absorbent layer beneath the backing layer.

16 Claims, 14 Drawing Sheets

(51) Int. Cl.
*A61F 13/02* (2006.01)
*A61L 15/24* (2006.01)
*A61L 15/58* (2006.01)

(52) U.S. Cl.
CPC ........ *A61M 1/0086* (2014.02); *A61M 1/0088* (2013.01); *A61L 15/24* (2013.01); *A61L 15/58* (2013.01); *A61M 2205/7536* (2013.01)

(58) Field of Classification Search
CPC .......... A61M 2205/7536; A61M 1/008; A61M 1/0088; A61M 25/02; A61L 15/24; A61L 15/58
See application file for complete search history.

(56) References Cited

U.S. PATENT DOCUMENTS

| | | | |
|---|---|---|---|
| 4,813,942 A | 3/1989 | Alvarez |
| 5,056,510 A | 10/1991 | Gilman |
| 5,181,905 A | 1/1993 | Flam |
| 5,238,732 A | 8/1993 | Krishnan |
| 5,549,584 A | 8/1996 | Gross |
| 5,707,499 A | 1/1998 | Joshi et al. |
| 5,759,570 A | 6/1998 | Arnold |
| 6,071,267 A | 6/2000 | Zamierowski |
| 6,626,891 B2 | 9/2003 | Ohmstede |
| 6,685,681 B2 | 2/2004 | Lockwood et al. |
| 6,752,794 B2 | 6/2004 | Lockwood et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,070,584 B2 | 7/2006 | Johnson et al. |
| 7,108,683 B2 | 9/2006 | Zamierowski |
| 7,216,651 B2 | 5/2007 | Argenta et al. |
| 7,361,184 B2 | 4/2008 | Joshi |
| 7,381,859 B2 | 6/2008 | Hunt et al. |
| 7,569,742 B2 | 8/2009 | Haggstrom et al. |
| 7,605,298 B2 | 10/2009 | Bechert et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,118,794 B2 | 2/2012 | Weston et al. |
| 8,152,785 B2 | 4/2012 | Vitaris |
| 8,162,907 B2 | 4/2012 | Heagle |
| 8,207,392 B2 | 6/2012 | Haggstrom et al. |
| 8,235,972 B2 | 8/2012 | Adahan |
| 8,241,261 B2 | 8/2012 | Randolph et al. |
| 8,282,611 B2 | 10/2012 | Weston |
| 8,303,552 B2 | 11/2012 | Weston |
| 8,372,049 B2 | 2/2013 | Jaeb et al. |
| 8,372,050 B2 | 2/2013 | Jaeb et al. |
| 8,425,478 B2 | 4/2013 | Olson |
| 8,444,612 B2 | 5/2013 | Patel et al. |
| 8,460,255 B2 | 6/2013 | Joshi et al. |
| 8,513,481 B2 | 8/2013 | Gergeley et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,628,505 B2 | 1/2014 | Weston |
| 8,641,691 B2 | 2/2014 | Fink |
| 8,663,198 B2 | 3/2014 | Buan et al. |
| 8,715,256 B2 | 5/2014 | Greener |
| 8,764,732 B2 | 7/2014 | Hartwell |
| 8,795,243 B2 | 8/2014 | Weston |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,956,336 B2 | 2/2015 | Haggstrom et al. |
| 9,012,714 B2 | 4/2015 | Fleischmann |
| 9,061,095 B2 | 6/2015 | Adie et al. |
| 9,067,003 B2 | 6/2015 | Buan et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,220,822 B2 | 12/2015 | Hartwell et al. |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,427,505 B2 | 8/2016 | Askem et al. |
| 9,446,178 B2 | 9/2016 | Blott et al. |
| 9,452,248 B2 | 9/2016 | Blott et al. |
| 9,629,986 B2 | 4/2017 | Patel et al. |
| 9,669,138 B2 | 6/2017 | Joshi et al. |
| 9,681,993 B2 | 6/2017 | Wu et al. |
| 9,795,725 B2 | 10/2017 | Joshi et al. |
| 9,808,561 B2 | 11/2017 | Adie et al. |
| 9,829,471 B2 | 11/2017 | Hammond et al. |
| 9,844,473 B2 | 12/2017 | Blott et al. |
| 9,956,121 B2 | 5/2018 | Hartwell |
| 9,962,474 B2 | 5/2018 | Greener |
| 2003/0125646 A1 | 7/2003 | Whitlock |
| 2004/0057855 A1 | 3/2004 | Gerlach et al. |
| 2006/0009744 A1 | 1/2006 | Edrman et al. |
| 2007/0040454 A1 | 2/2007 | Freudenberger et al. |
| 2007/0055209 A1 | 3/2007 | Patel et al. |
| 2007/0225663 A1 | 9/2007 | Watt et al. |
| 2008/0031748 A1 | 2/2008 | Ihle et al. |
| 2008/0132821 A1 | 6/2008 | Propp et al. |
| 2008/0306456 A1 | 12/2008 | Riesinger |
| 2009/0125004 A1 | 5/2009 | Shen et al. |
| 2009/0157024 A1 | 6/2009 | Song |
| 2009/0234306 A1 | 9/2009 | Vitaris |
| 2009/0299251 A1 | 12/2009 | Buan |
| 2009/0299306 A1 | 12/2009 | Buan |
| 2010/0125258 A1 | 5/2010 | Coulthard et al. |
| 2010/0259406 A1 | 10/2010 | Caso et al. |
| 2010/0318052 A1 | 12/2010 | Ha et al. |
| 2011/0004172 A1 | 1/2011 | Eckstein et al. |
| 2011/0118683 A1 | 5/2011 | Weston |
| 2011/0224631 A1 | 9/2011 | Simmons |
| 2012/0051945 A1 | 3/2012 | Orndorff et al. |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0150814 A1 | 6/2013 | Buan |
| 2013/0165878 A1 | 6/2013 | Heagle |
| 2013/0165881 A1* | 6/2013 | Boothman .......... A61F 13/0223 604/369 |
| 2013/0274688 A1 | 10/2013 | Weston |
| 2013/0302545 A1 | 11/2013 | Schnelker et al. |
| 2014/0114268 A1 | 4/2014 | Auguste et al. |
| 2014/0303575 A1 | 10/2014 | May |
| 2014/0316359 A1 | 10/2014 | Collinson et al. |
| 2015/0032035 A1 | 1/2015 | Banwell et al. |
| 2015/0065965 A1 | 3/2015 | Haggstrom et al. |

(56) References Cited

U.S. PATENT DOCUMENTS

| | | | |
|---|---|---|---|
| 2015/0119831 A1 | 4/2015 | Robinson et al. | |
| 2015/0119832 A1 | 4/2015 | Locke | |
| 2015/0119833 A1 | 4/2015 | Coulthard et al. | |
| 2016/0000611 A1 | 1/2016 | Niederauer et al. | |
| 2016/0081859 A1 | 3/2016 | Hartwell | |
| 2016/0136339 A1 | 5/2016 | Begin et al. | |
| 2016/0144084 A1 | 5/2016 | Collinson et al. | |
| 2016/0193452 A1* | 7/2016 | Hanson | A61M 25/02 602/52 |
| 2016/0298620 A1 | 10/2016 | Cordoba et al. | |
| 2016/0317357 A1 | 11/2016 | Vitaris et al. | |
| 2016/0374860 A1 | 12/2016 | Revol-Cavalier et al. | |
| 2017/0128642 A1 | 5/2017 | Buan | |
| 2017/0181896 A1 | 6/2017 | Hartwell | |
| 2017/0181897 A1 | 6/2017 | Hartwell | |
| 2017/0368239 A1 | 12/2017 | Askem et al. | |
| 2018/0133378 A1 | 5/2018 | Askem et al. | |
| 2018/0221548 A1 | 8/2018 | Jaeb et al. | |
| 2018/0318476 A1 | 11/2018 | Askem et al. | |
| 2020/0121833 A9 | 4/2020 | Askem et al. | |

FOREIGN PATENT DOCUMENTS

| | | | |
|---|---|---|---|
| EP | 0 257 916 | 3/1988 | |
| EP | 0 340 018 | 11/1989 | |
| EP | 1 476 217 | 3/2008 | |
| EP | 1 955 887 | 8/2008 | |
| EP | 2 462 908 | 6/2012 | |
| EP | 2 544 642 | 1/2015 | |
| EP | 2 648 668 | 1/2015 | |
| FR | 1 163 907 | 10/1958 | |
| GB | 1255395 | 12/1971 | |
| WO | WO 1983/00742 | 3/1983 | |
| WO | WO 1995/029959 | 11/1995 | |
| WO | WO 1996/05873 | 2/1996 | |
| WO | WO 2004/077387 | 9/2004 | |
| WO | WO 2005/025447 | 3/2005 | |
| WO | WO 2005/123170 | 12/2005 | |
| WO | WO 2006/052839 | 5/2006 | |
| WO | WO 2008/039223 | 4/2008 | |
| WO | WO 2009/066105 | 5/2009 | |
| WO | WO 2009/124100 | 10/2009 | |
| WO | WO 2009/158128 | 12/2009 | |
| WO | WO 2010/142959 | 12/2010 | |
| WO | WO 2011/135285 | 11/2011 | |
| WO | WO 2011/135286 | 11/2011 | |
| WO | WO 2011/135287 | 11/2011 | |
| WO | WO 2011/144888 | 11/2011 | |
| WO | WO 2012/041296 | 4/2012 | |
| WO | WO 2012/131237 | 10/2012 | |
| WO | WO 2012/140378 | 10/2012 | |
| WO | WO 2012/143665 | 10/2012 | |
| WO | WO 2013/010907 | 1/2013 | |
| WO | WO 2013/064852 | 5/2013 | |
| WO | WO 2013/083800 | 6/2013 | |
| WO | WO 2013/090810 | 6/2013 | |
| WO | WO 2013/136181 | 9/2013 | |
| WO | WO 2013/149078 | 10/2013 | |
| WO | WO 2014/008348 | 1/2014 | |
| WO | WO 2014/016759 | 1/2014 | |
| WO | WO 2014/020440 | 2/2014 | |
| WO | WO 2014/020443 | 2/2014 | |
| WO | WO 2014/108476 | 7/2014 | |
| WO | WO 2014/113253 | 7/2014 | |
| WO | WO 2014/140608 | 9/2014 | |
| WO | WO-2014140608 A1 * | 9/2014 | A61F 13/0216 |
| WO | WO 2015/022334 | 2/2015 | |
| WO | WO 2015/022340 | 2/2015 | |
| WO | WO 2015/031216 | 3/2015 | |
| WO | WO 2016/018448 | 2/2016 | |
| WO | WO 2016/184916 | 11/2016 | |
| WO | WO-2016174048 A1 | 11/2016 | |

OTHER PUBLICATIONS

Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

Kendall ULTEC Hydrocolloid Dressing (4"x4"), product ordering page, web page downloaded Jul. 13, 2014, in 1 page.

Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.

Protz, Kerstin: "Moderne Wundauflagen unterstutzen Heilungsprozess", Wundversorgung: Indikation and Anwendung, Geriatrie Journal, Apr. 2005, pp. 3333-3339, with translation, in 17 pages.

Smith & Nephew, "PICO Single Use Negative Pressure Wound Therapy System", spiral booklet, Mar. 2011, in 7 pages.

International Search Report and Written Opinion, re PCT Application No. PCT/IB2016/001959, dated Apr. 18, 2017.

International Preliminary Report on Patentability for Application No. PCT/IB2016/001959, dated Jul. 12, 2018, 8 pages.

* cited by examiner

ABSORBENT NEGATIVE PRESSURE WOUND THERAPY DRESSING

CROSS-REFERENCE TO RELATED APPLICATIONS

CROSS-REFERENCE TO RELATED APPLICATIONS

This application is a U.S. national stage application of International Patent Application No. PCT/IB2016/001959, filed on Dec. 30, 2016, which claims the benefit of U.S. Provisional Application No. 62/273,053, filed Dec. 30, 2015, entitled ABSORBENT NEGATIVE PRESSURE WOUND THERAPY DRESSING. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

BACKGROUND OF THE INVENTION

Field of the Invention

Embodiments of the present invention relate generally to the treatment of wounds using negative pressure wound therapy, in particular the prevention of fluid absorption in selected regions of a negative pressure wound therapy dressing.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

However, in some wound dressings the absorbent layer fills up with fluid in an unpredictable, and often, non-uniform manner. It may be desirable, in some situations, to more easily prevent fluid from reaching certain areas of the absorbent layer or of the overall dressing. Current dressings have limited and/or unsatisfactory methods of controlling fluid paths in the absorbent layer and/or throughout the dressing.

SUMMARY OF THE INVENTION

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein.

According to some embodiments there is provided a wound treatment apparatus for treatment of a wound site, the wound treatment apparatus comprising: a wound dressing configured to be positioned over a wound site, the wound dressing comprising: a backing layer having an upper surface and a lower surface and defining a perimeter configured to be positioned over skin surrounding the wound site, the backing layer including an opening; adhesive or glue located on an upper surface of the backing layer; and an absorbent layer configured to be positioned between the backing layer and the wound site.

In embodiments, the wound treatment apparatus may further comprise a wound contact layer beneath the absorbent layer and sealed to the backing layer. In certain embodiments, an apparatus may further comprise a source of negative pressure configured to be in fluid communication with the wound site through the wound dressing. The absorbent material may comprise a vertical hole positioned below the opening in the backing layer. In particular embodiments, the wound treatment apparatus may further comprise a fluidic connector. The glue may be positioned between the backing layer and the distal end of the fluidic connector. In embodiments, the glue may be positioned on the upper surface of the backing layer spaced away from the fluidic connector. The glue may be configured to prevent passage of liquid within the absorbent layer. In certain embodiments, the glue may be a cyanoacrylate adhesive.

In certain aspects, the glue is located on an upper surface of the backing layer and positioned over the periphery of the absorbent layer. The glue may be positioned over one edge of the absorbent layer. The glue may be positioned in a stripe across the width of the absorbent layer. In embodiments, the glue is positioned in four stripes across the width of the absorbent layer. The glue may be positioned in a square pattern around the distal end of the fluidic connector.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

DETAILED DESCRIPTION OF THE PREFERRED EMBODIMENTS

Figure 1A:
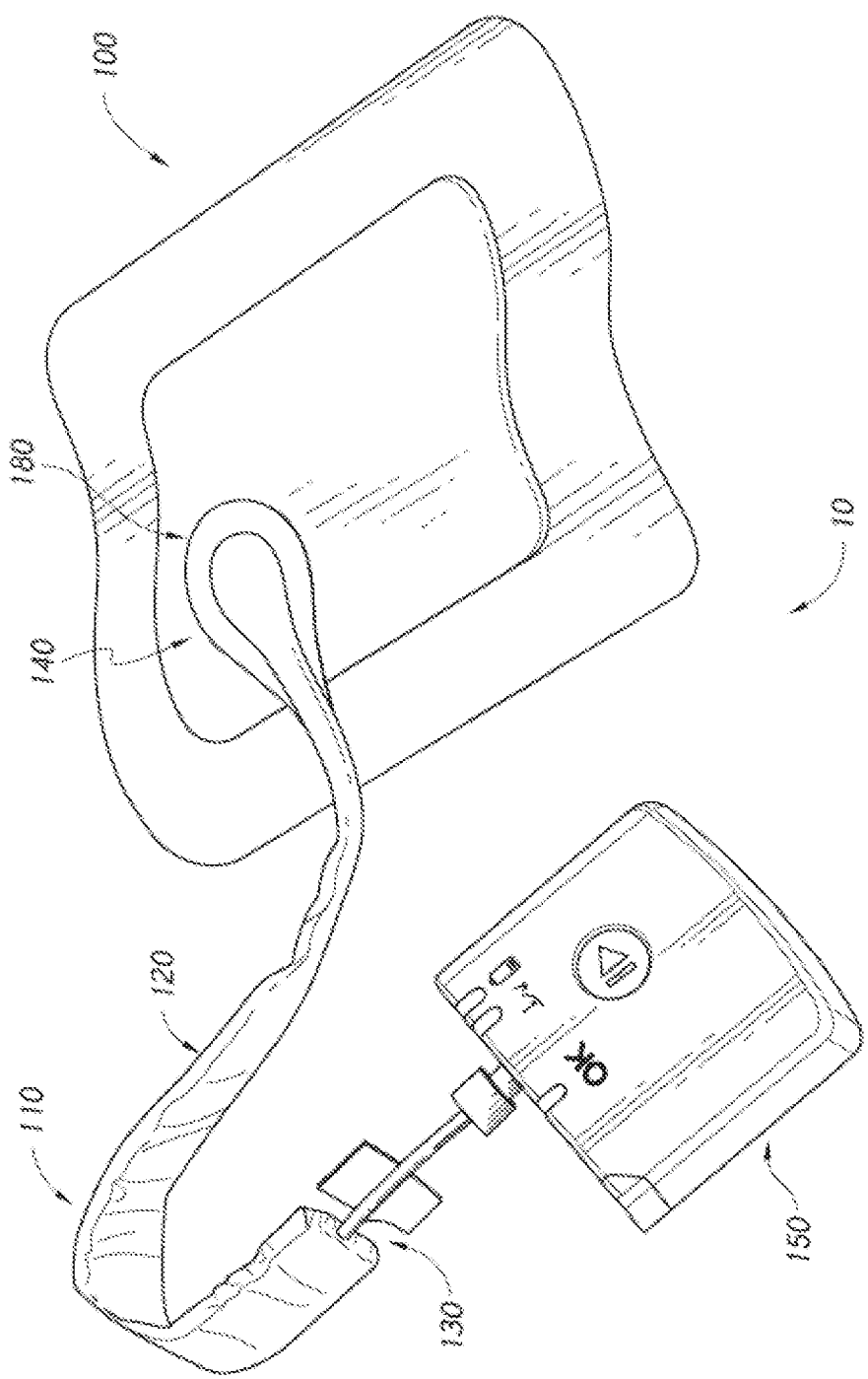
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds. Certain embodiments of this application relate to a wound treatment apparatus employing a wound dressing and a fluidic connector, and to methods of using the same.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 mmHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,874, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in International Application No. PCT/EP2016/059329, filed Apr. 26, 2016, published as WO2016174048 A1 on Nov. 3, 2016, titled "REDUCED PRESSURE APPARATUS AND METHODS."

The Wound Dressings of FIGS. 1A-2B

Figure 1B:
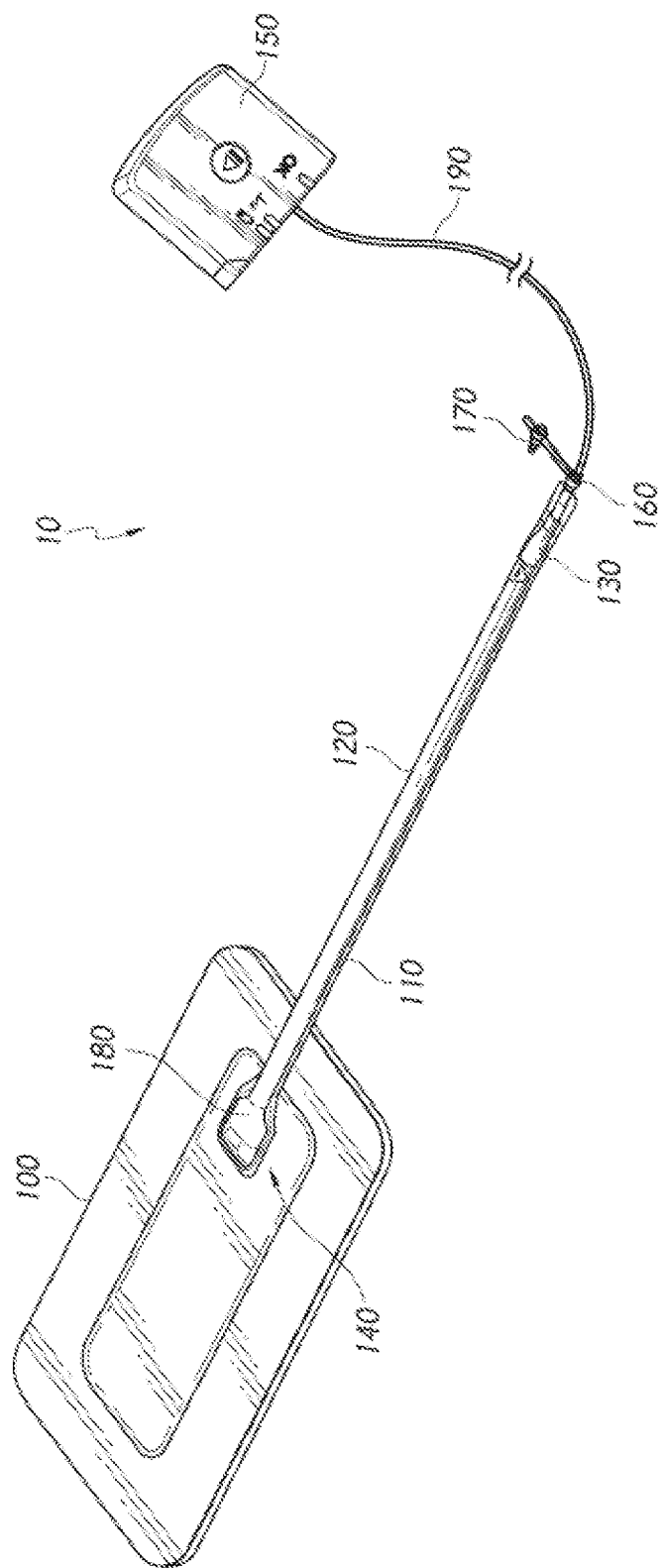
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved. In some embodiments, the pump can be miniaturized and portable, although larger conventional pumps may also be used with the dressing 100. In some embodiments, the pump may be attached or mounted onto or adjacent the dressing 100.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include a cover layer for positioning over the layers of the wound dressing. The cover layer can be the upper most layer of the dressing. In some embodiments, the wound dressing can include a second cover layer for positioning over the layers of the wound dressing and any of the integrated components. The second cover layer can be the upper most layer of the dressing or can be a separate envelope that encloses the integrated components of the topical negative pressure system.

Figure 2A:
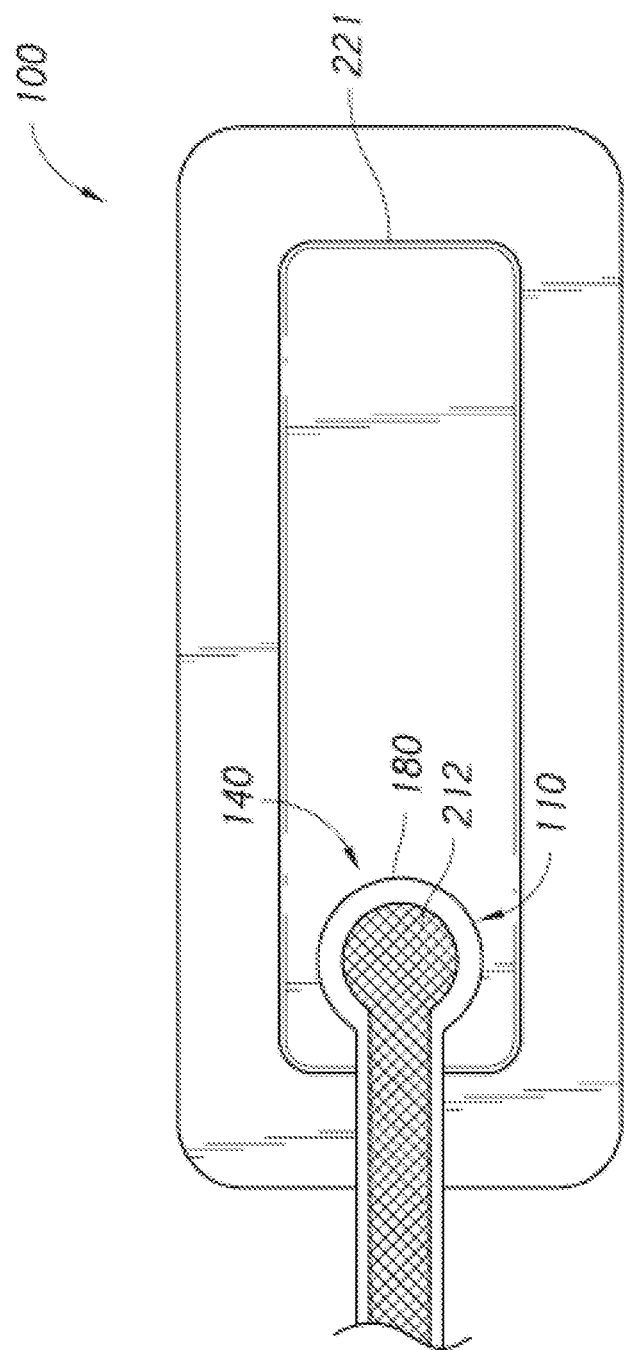
FIG. 2A illustrates an embodiment of a negative pressure wound treatment system employing a flexible fluidic connector and a wound dressing capable of absorbing and storing wound exudate.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 100 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 2B:
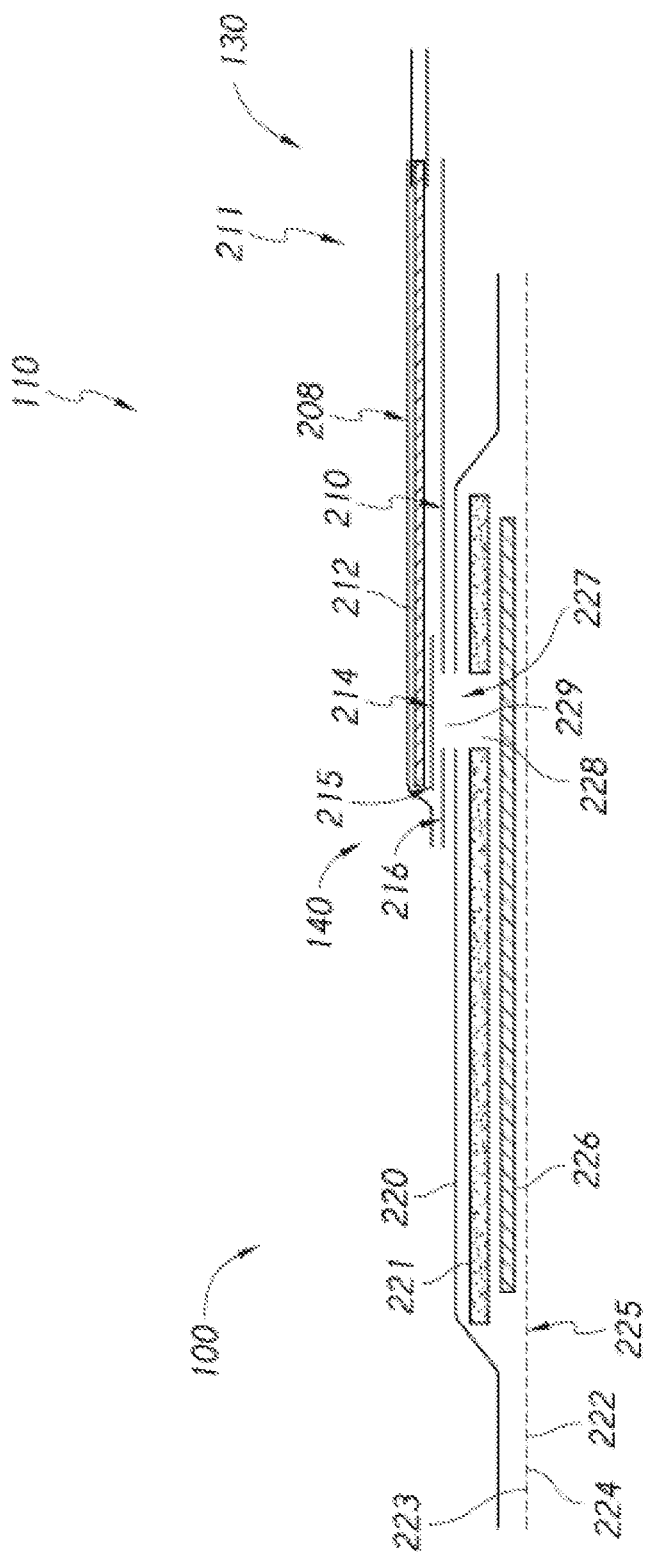
FIG. 2B illustrates a cross section of an embodiment of a fluidic connector connected to a wound dressing.

FIG. 2B illustrates a cross-section through a wound dressing 100 similar to the wound dressing 100 as shown in FIG. 113 and described in International Patent Publication WO2013175306 A2, filed May 22, 2013, entitled "APPARATUSES AND METHODS FOR NEGATIVE PRESSURE WOUND THERAPY", the disclosure of which is hereby incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 While also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in US Patent Publication 2015/0190286 A1, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 110, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 (described below) may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected to the sealing surface 216. The filter 214 is configured to substantially prevent wound exudate from entering the bridge.

Some embodiments may further comprise an optional second fluid passage positioned above the first fluid passage 212. For example, some embodiments may provide for an air leak may be disposed at the proximal end of the top layer 208 that is configured to provide an air path into the first fluid passage 212 and dressing 100 similar to the suction adapter as described in U.S. Pat. No 8,801,685, filed Dec. 30, 2011, entitled "APPARATUSES AND METHODS FOR NEGATIVE PRESSURE WOUND THERAPY" the disclosure of which is hereby incorporated by reference in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 µm. Suitable materials for the filter material of the filter element 214 include 0.2 micron Gore™ m expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

The Wound Dressing Embodiments of FIGS. 3A-5

In certain embodiments, such as described above in relation to FIG. 2B, fluid (for example, wound exudate) is handled by the dressing 100 by passing through the perforated wound contact layer 222, into the transmission layer 226, and is then absorbed and retained by the absorbent layer 221. Fluid is then able to evaporate through the breathable backing layer 220. However, in some embodiments, such as those observed during in vitro wound model testing, the absorbent layer fills up with fluid in an unpredictable, and often, non-uniform manner. Therefore, as described above, it may be desirable to prevent fluid from reaching certain areas of the absorbent layer.

In certain embodiments, fluid saturation of the absorbent layer may be impeded by applying a glue such as a cyanoacrylate Super Glue (for example Loctite, by Henkel) onto the backing layer. Herein this section and throughout the specification, the term "glue" will be used to indicate an adhesive such as Super Glue or any cyanoacrylate glue. Further, adhesives that may be indicated by the use of the term "glue" include hydrophobic adhesives and adhesives that evolve or release a gas containing hydrophobic materials.

Application of the glue affects the underlying absorbent layer by preventing liquid from being absorbed in the area below the glue. In some embodiments, the glue prevents certain areas of the absorbent material from swelling with fluid, thereby acting as a liquid barrier. Glue may be applied to the backing layer or elsewhere in the dressing via any suitable method, such as via an applicator tube and/or spray bottle. As will be understood by one of skill in the art, glue could be applied to the cover layer, absorbent layer, wound contact layer, and/or the transmission layer in any manner described herein this section or elsewhere in the specification.

Application of the glue to the topmost cover layer allows gaseous material from the glue to pass through the top film into the absorbent layer. Such gaseous material may alter the hydrophobicity of the underlying absorbent layer, thereby affecting the fluid passage through and within the absorbent layer. In embodiments, the gaseous material may deposit a hydrophobic residue on the fibers of the absorbent layer.

Figure 3A:
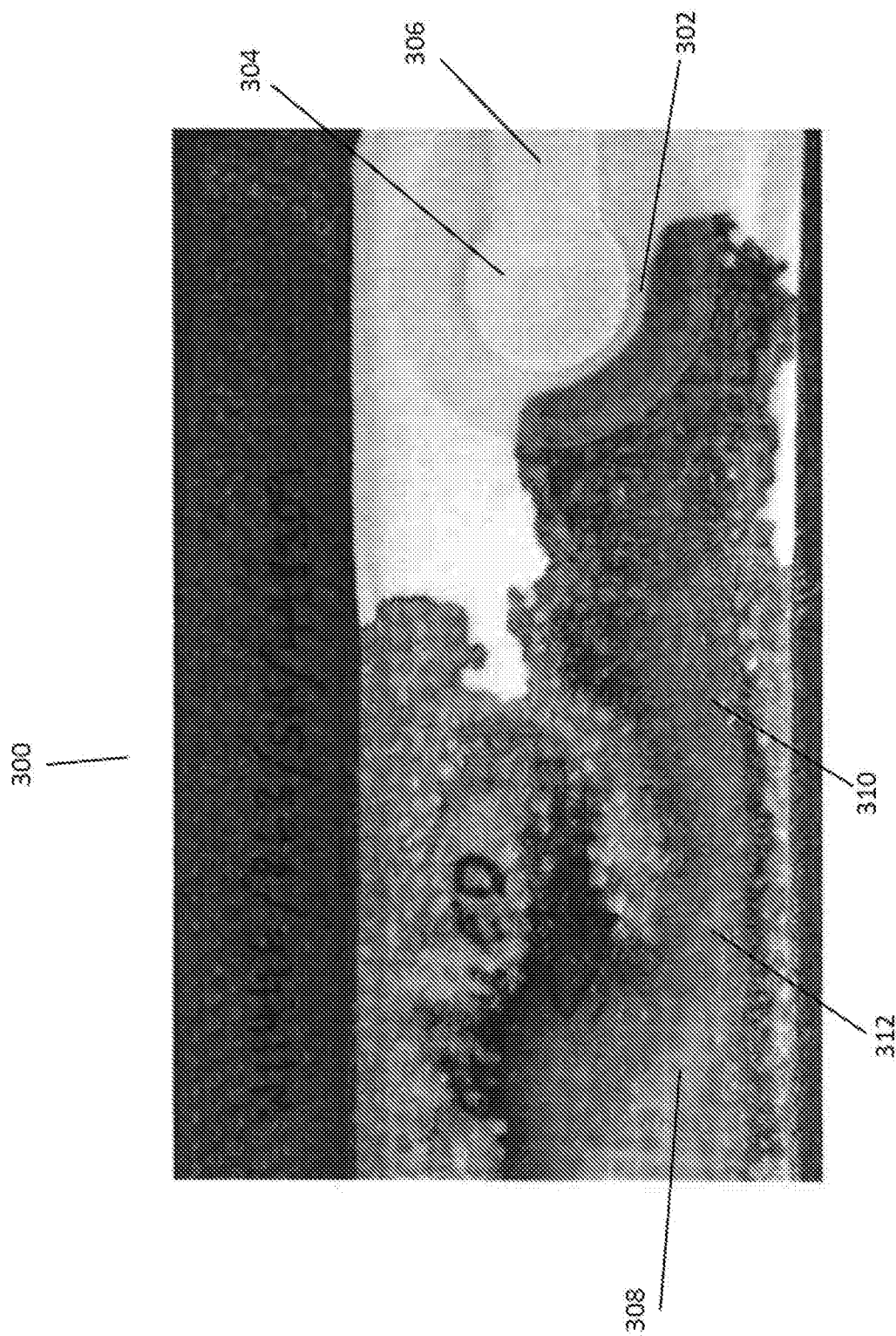
FIG. 3A is an image of an embodiment of a partially saturated wound dressing, comprising a ring of glue around the distal end of a fluidic connector.
Figure 3B:
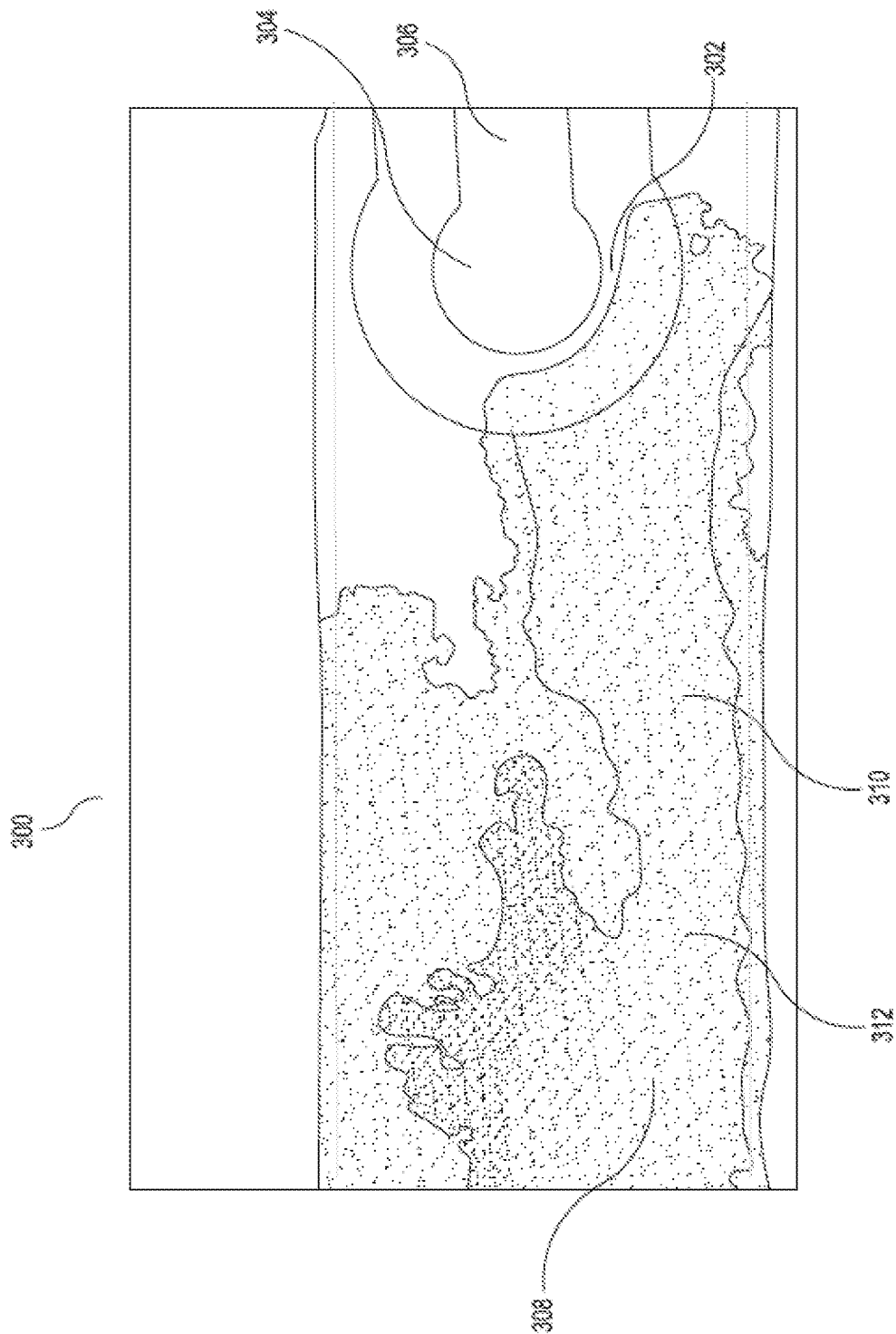
FIG. 3B is an illustration of an embodiment of a partially saturated wound dressing, comprising a ring of glue around the distal end of a fluidic connector.

FIGS. 3A-3B show a top view of an embodiment of a wound dressing 300, similar to the dressings described in FIGS. 2A-2B, with a ring of glue 302 that adheres the distal end 304 of the fluidic connector 306 to dressing 300. FIG. 3A is a photograph of the topside of the embodiment of the wound dressing while FIG. 3B is an illustration of the same. Liquid was drawn into the dressing 308 and is visible through the backing layer 310 saturating the absorbent layer 312. However, the liquid bends around the ring of glue 302, even though the glue has been applied to the top of the backing layer 310. In embodiments, application of glue to the top of the backing layer may beneficially prevent areas of the underlying absorbent layer 312 from becoming saturated and swollen. In embodiments, this prevention of saturation is beneficial as swelling of super absorber particles in this area can occlude the fluidic connection 306, therefore preventing negative pressure delivery.

In certain embodiments, the glue may be located at a variety of locations on the backing layer. For example, the glue may be applied all the way to the edge of the opening in the backing layer and/or cover the entire distal end of the fluidic connector to the outer edge of the fluidic connector. As described above, the glue may be applied around the rim of the opening in the form of a ring. In embodiments, the glue may be applied as a single line or as a series of lines. The glue may be applied as a spiral or as concentric circles on the backing layer. In certain embodiments, the glue may be applied as distinct, single lines or multiple lines. The glue may be applied to the underside of the backing layer in any manner described in relation to the topside of the backing layer.

In embodiments, the glue may be applied around the periphery of the backing layer, for example, the entire periphery, 50% of the entirety, or 25% of the entirety. In certain embodiments the glue may be applied to only a portion of the perimeter of the distal end fluidic connector, for example 25%, 50%, or 75%. The glue may be applied to create channels in the underlying absorbent layers to channel wound exudate to the opening in the backing layer. In certain embodiments, the glue may be applied under the applicator portion of the fluidic connector, but not the fluid passage. In embodiments, the glue may be applied to only the outermost ring of the applicator portion of the fluidic connector and/or the glue may be applied to the sealing surface of the fluidic connector. In further embodiments, the glue may be applied on the backing layer around but not under the fluidic connector.

In certain embodiments, the glue may be applied directly to the absorbent layer in any manner described herein this section or elsewhere in the specification, particularly as described above in relation to the backing layer. In some embodiments, the glue may be applied directly to the transmission layer in any manner described herein this section or elsewhere in the specification, particularly as described above in relation to the backing layer. In embodiments, the glue may be applied directly to the wound contact layer in any manner described herein this section or elsewhere in the specification, particularly as described above in relation to the backing layer.

Figure 4A:
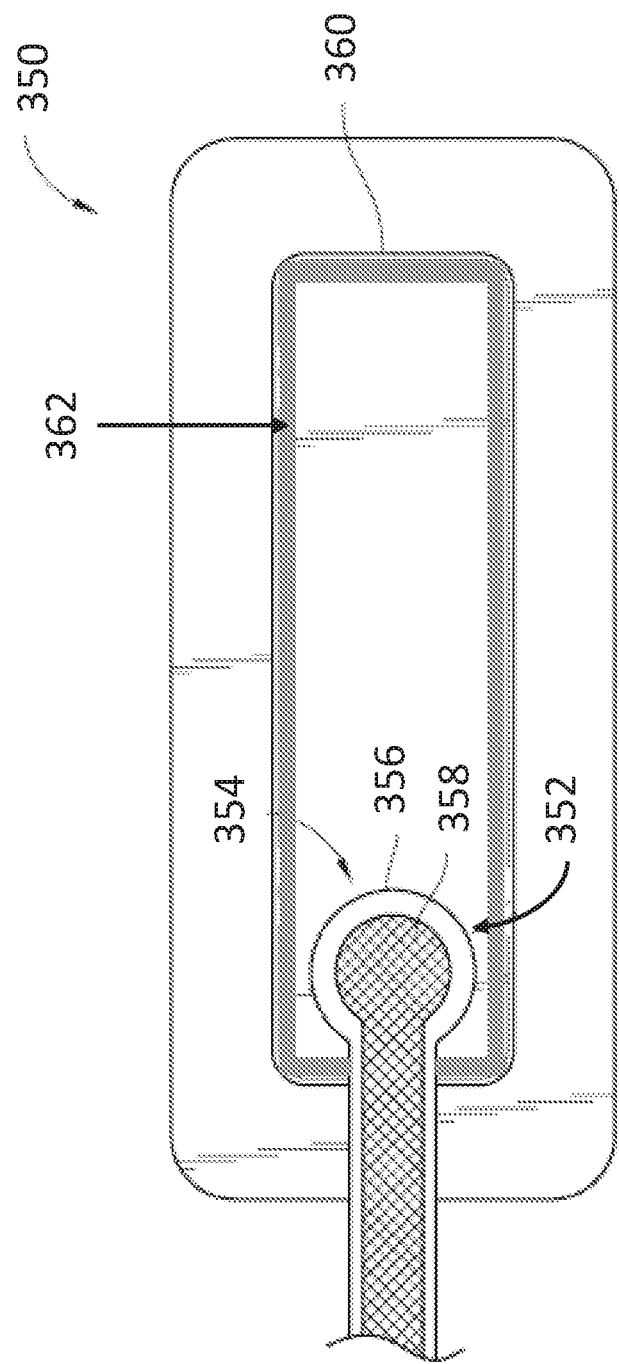
FIGS. 4A-C are illustrations of embodiments of wound dressings with various patterns of glue.
Figure 4B:
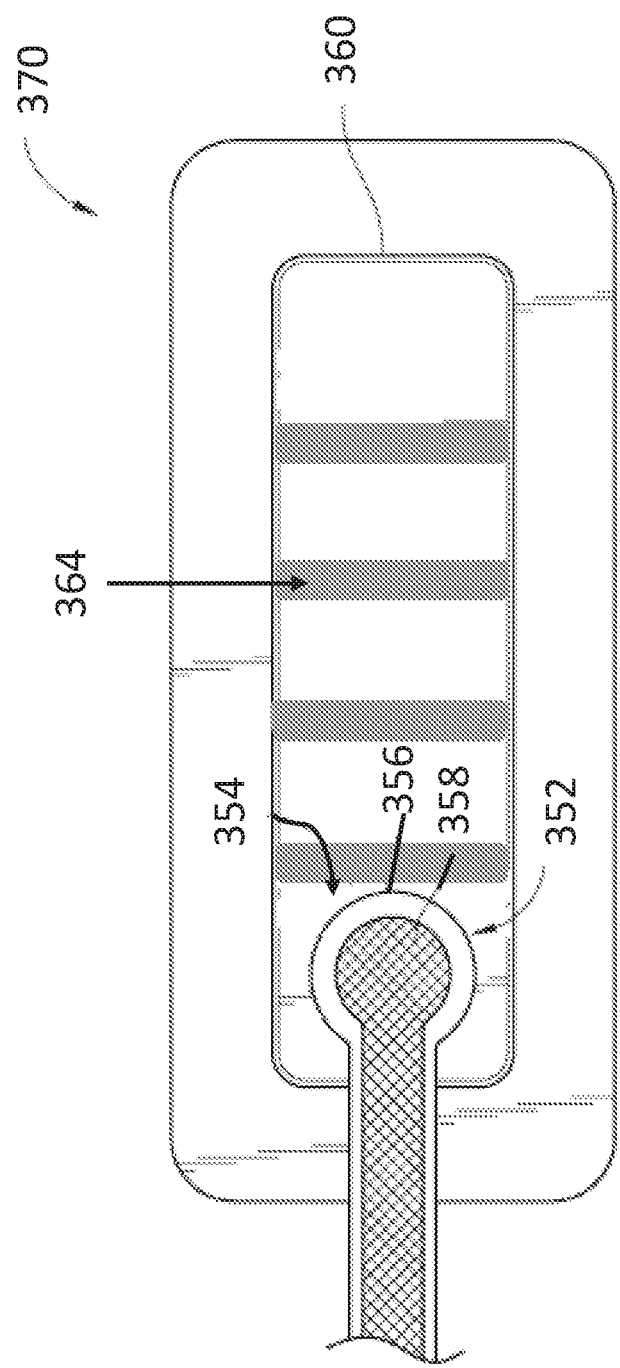
Figure 4C:
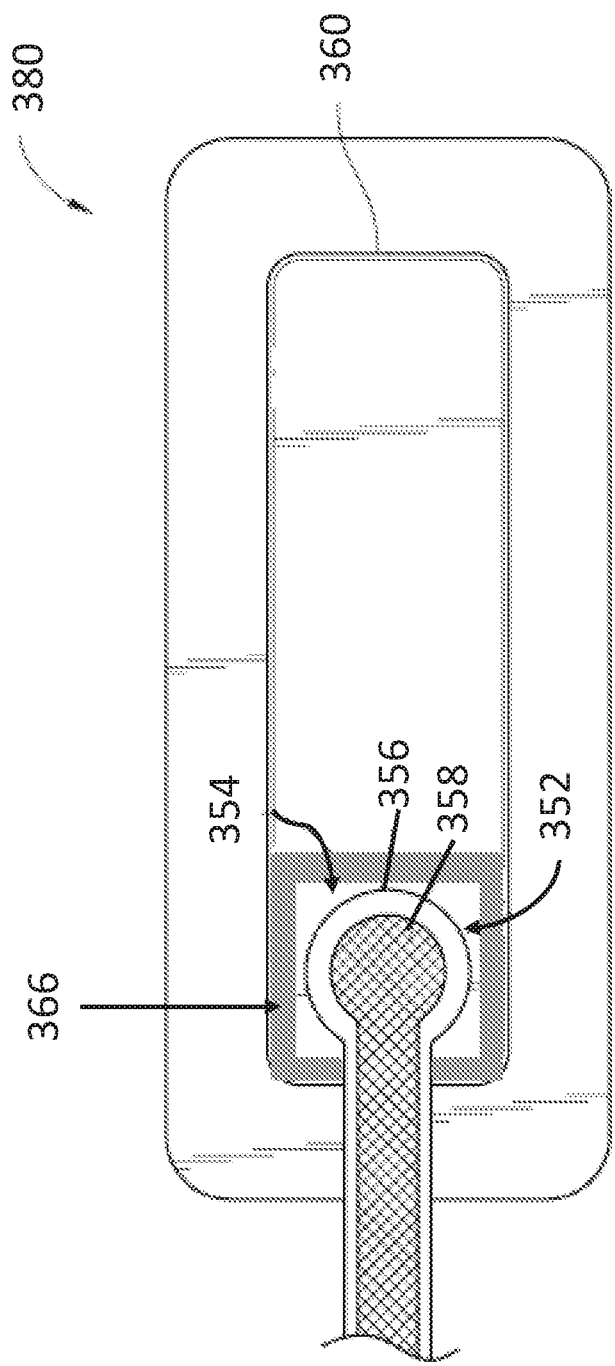

FIGS. 4A-4C are illustrations of embodiments of wound dressings with glue applied in different patterns to the cover layers. However, as will be understood by one of skill in the art, glue may be applied in the same or similar patterns to any portion of the wound dressing, for example: the absorbent layer, the wound contact layer, and/or the transmission layer.

FIGS. 4A-4C depict embodiments of wound dressings 350, 370, 380 similar to the dressing of FIGS. 2A and 2B. As in FIG. 2A, the wound dressings of FIGS. 4A-4C may have a fluidic connector 352, distal end 354, applicator 356, fluid passage 358, and absorbent layer 360. However, in embodiments, the wound dressing 350 may contain a layer of glue 362 such as disclosed herein this section or elsewhere in the specification. The layer of glue 362 may be applied to the areas of the backing layer overlying the outer edge of the absorbent layer, thereby creating a liquid barrier at the peripheral edge of the underlying absorbent layer. In embodiments, the glue may be applied to portions of the backing layer above the entirety of the outer periphery of the absorbent layer. Alternatively, the glue may be applied to the backing layer overlying only one edge, two edges, or three edges of the underlying absorbent layer. Advantageously, applying glue to the backing layer over the edges of the absorbent layer may prevent fluid leakage from the absorbent layer into the remainder of the dressing.

FIG. 4B depicts an embodiment of a wound dressing similar to the dressing of FIG. 4B; however, here the glue may be placed in a different pattern, in stripes 364 across the width of the backing layer overlying the absorbent layer. The stripes may also be applied vertically, whereby they are aligned with the length of the wound dressing. The stripes may be curved such that the stripes present a concave or a convex side toward the distal end 354. In certain embodiments, the dressing may have one stripe, two stripes, three stripes, four stripes, five stripes, six stripes, ten stripes, or more than ten stripes. FIG. 4C depicts an embodiment of a wound dressing similar to the embodiments of FIGS. 4A, 4B, and 3A-B. Here the glue 366 is applied as a square around fluidic connector 352.

As described previously, one of skill in the art will also understand that the glue could be applied directly to the absorbent layer, the transmission layer, and/or the wound contact layer in similar patterns as disclosed above in relation to FIGS. 4A-4C.

Figure 5:
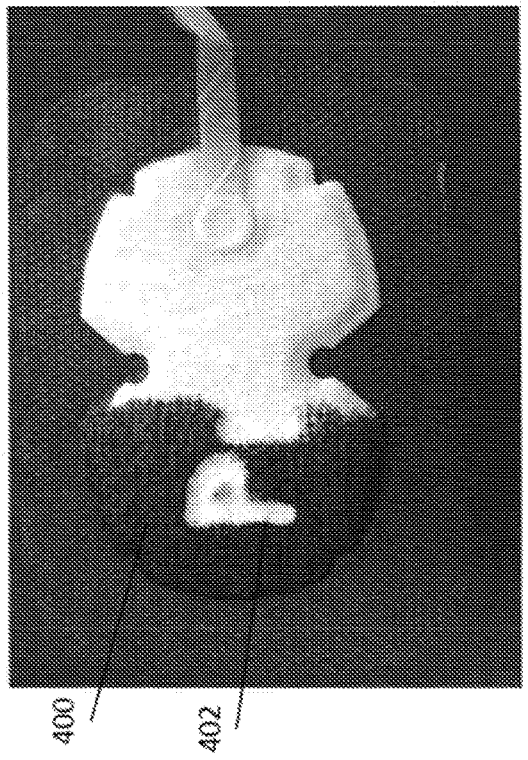
FIG. 5 shows multiple images of embodiments of a wound dressing that becomes more saturated with dyed fluid over time.
Figure 5:

FIG. 5 shows two images of an embodiment of a wound dressing 400, similar to the dressings of FIGS. 2A-4C. Here, a thin bead of super glue was used to write "PICO" on the dressing 402, specifically to the top of the backing layer. The dressing was then filled with a dye solution 404 which gradually revealed the word "PICO" written on the backing layer of the dressing. Similar to the glue ring shown in FIGS. 3A-B, application of glue to the top of the backing layer prevented areas of the underlying absorbent layer from becoming saturated. In certain embodiments, application of glue may be used to purposefully prevent areas of an absorbent layer (for example, around the distal end of the fluidic connector) from becoming saturated.

The Microscopic Images of FIGS. 6-9

FIGS. 6-9 are images of embodiments of dressings similar to the dressings of FIGS. 2A-4. The dressings were sectioned using a clean pair of scissors and a single edge razor blade. These images were motivated by certain observations of in vitro wound dressings. After application of glue to the port of a PICO dressing, it was observed that in a wound model the glued area appeared to repel horse serum, which would normally track to the port and block the port, often before the dressing was full. For the above observation, the glue was applied between the port and the top film of the dressing and around the cut edges of a hole in the absorbent layer directly underneath the soft port.

Figure 6:
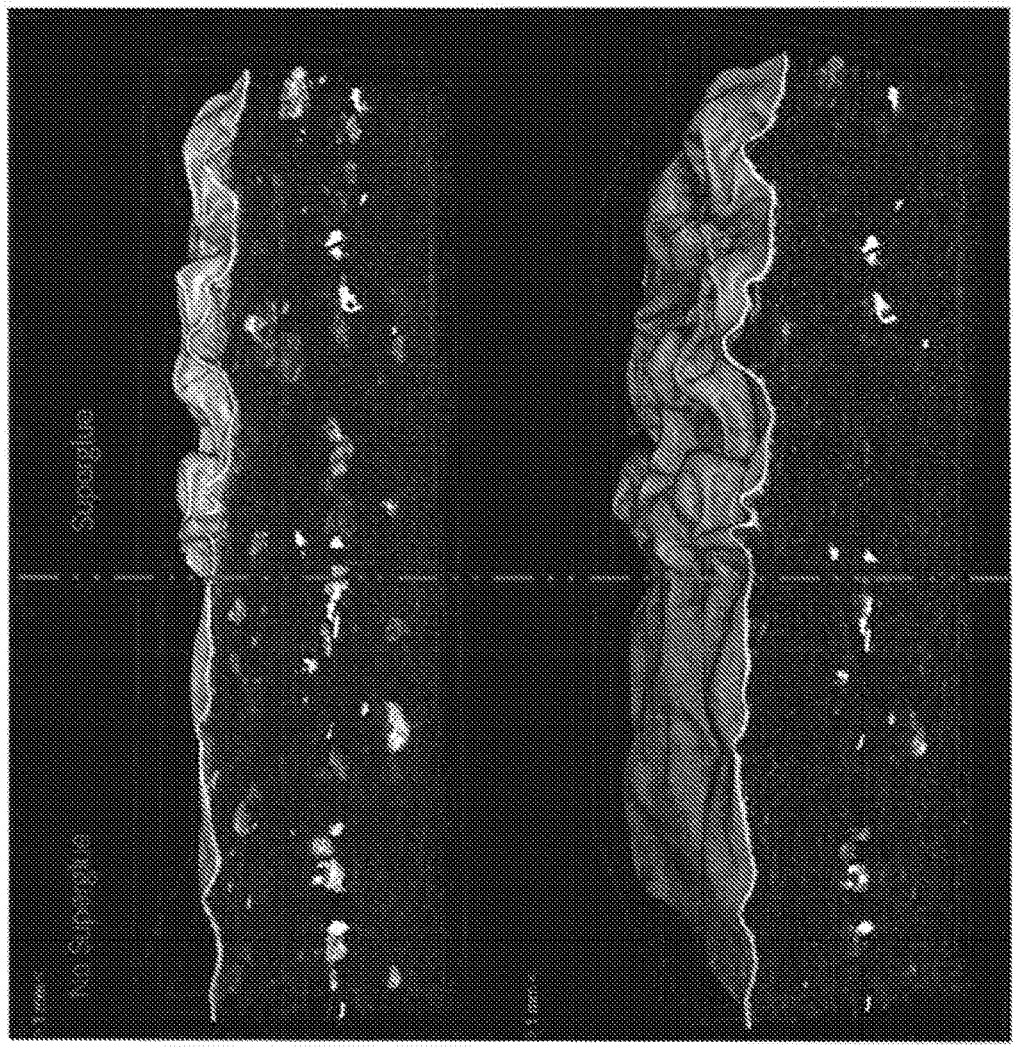
FIG. 6 shows multiple cross-sectional micro-CTs of embodiments of wound dressings with glue on the backing layer.

FIG. 6 shows micro-CT images, at two cross-sectional angles, of embodiments of a dressing 500 similar to the dressings of FIGS. 2A-4C. Here, glue applied over the backing layer of a section of dressing is compared side-by-side with a section of dressing with a backing layer with no glue. Apart from the textured appearance of the top film on the glue areas there were no macro structural differences between the areas with and without glue, in that there is no distinct sign of the fibers being bound together.

Figure 7:
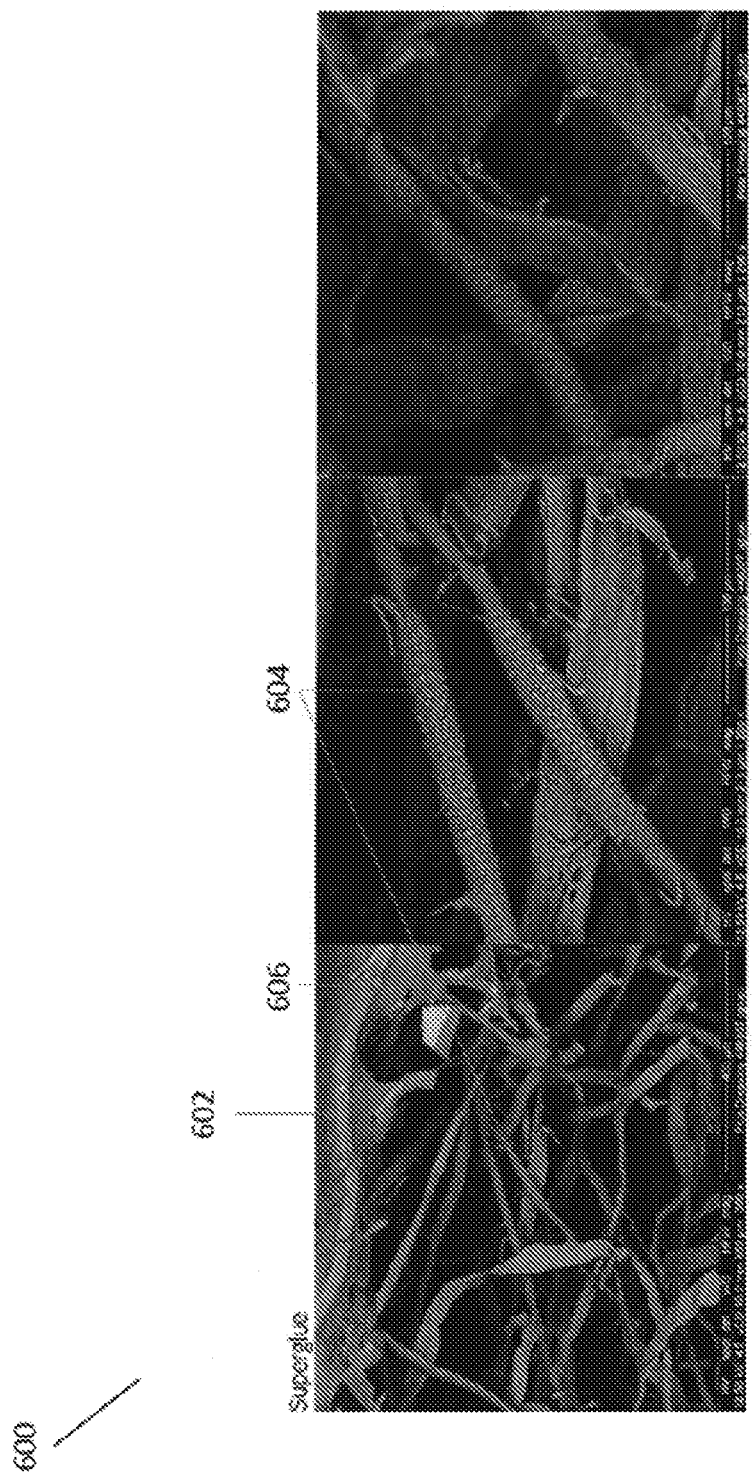
FIG. 7 shows multiple scanning electron microscopy (SEM) micrographs of embodiments of wound dressings with glue on the backing layer.

FIG. 7 is a series of SEM images of an embodiment of a dressing similar to the dressings of FIGS. 2A-5. Here, the backing layer was coated in glue 602. Inspection of the dressing section coated with glue did show that under the backing layer (with the glue) there were a number of fibers 604 and a section of a superabsorber particle (shown in FIG. 7) which had been coated with granular particulates. These granular particulates are likely hydrophobic residue from the gaseous material emitted by the glue. The granular particulates were not observed on the flat cellulosic fibers. FIG. 6 further includes construction adhesive 606 which was identified based on previous knowledge of similar dressings.

Figure 8:
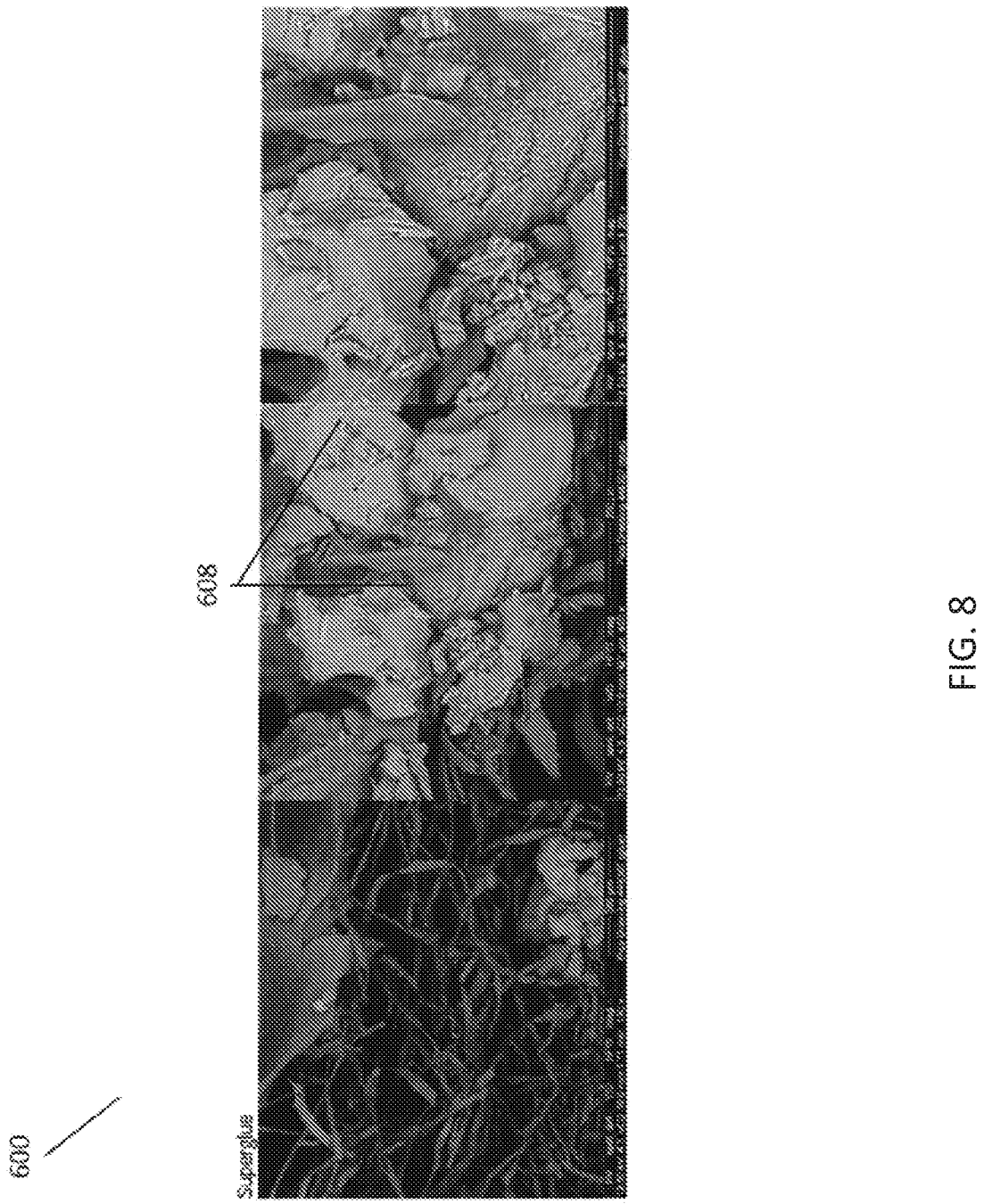
FIG. 8 shows multiple SEM micrographs of embodiments of wound dressings with glue on the backing layer.
Figure 9:
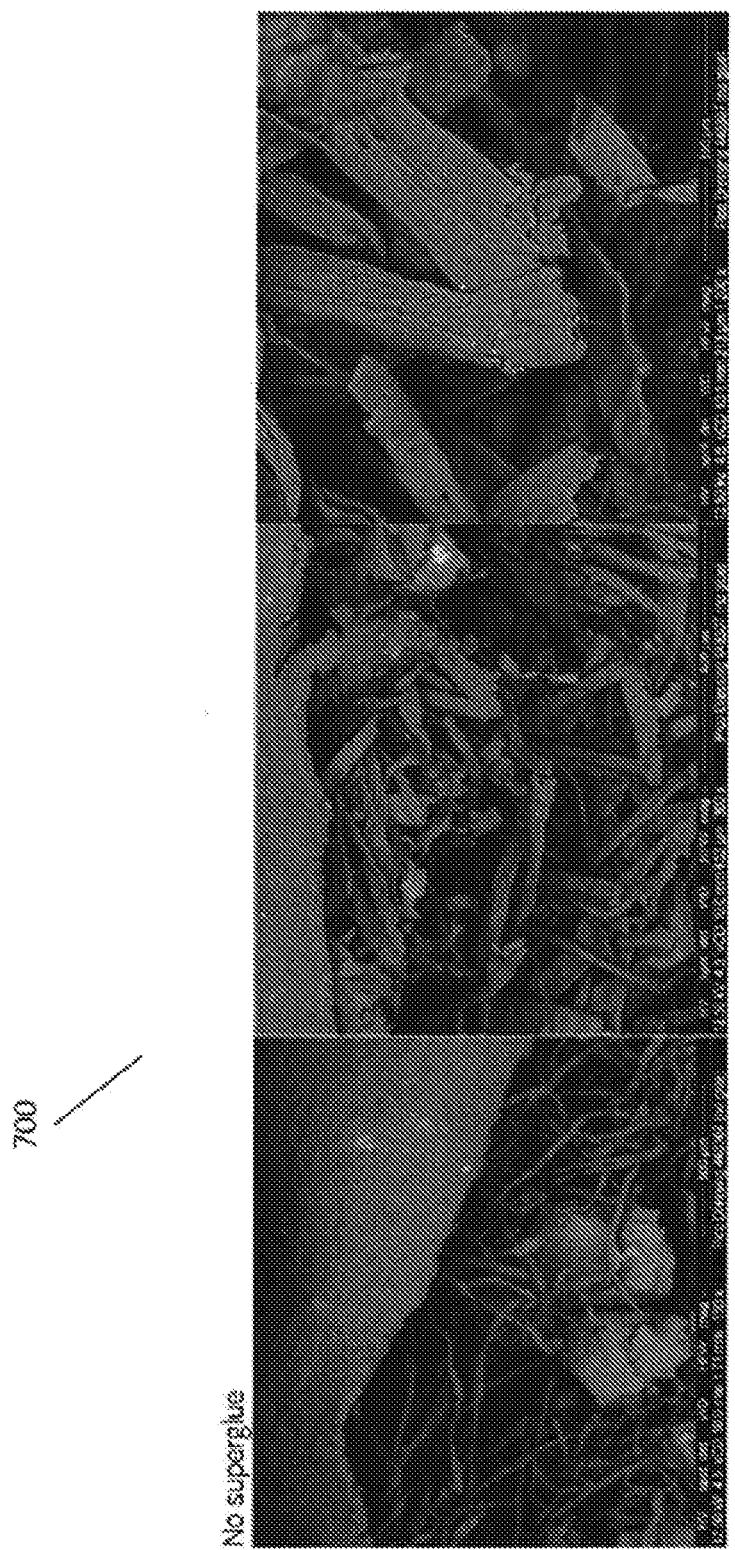
FIG. 9 shows multiple SEM micrographs of embodiments of wound dressings without glue on the backing layer.

FIG. 8 is a further series of SEM images of the wound dressing of FIG. 7. As in FIG. 7, glue has been applied to the backing layer of the dressing. Here, granular particulates 608 cover sections of super absorbent particles, again indicating the presence of materials released from the glue. FIG. 9 is a series of SEM images of a wound dressing 700, similar to the dressings of FIGS. 7-8, however here no superglue has been applied and no granular particulates are observed.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus for treatment of a wound site, comprising:
    a wound dressing configured to be positioned over a wound site, the wound dressing comprising:
        a backing layer having an upper surface and a lower surface and defining a perimeter configured to be positioned over skin surrounding the wound site, the backing layer including an opening;
        a fluidic connector, positioned on the upper surface of the backing layer;
        a cyanoacrylate adhesive located on an upper surface of the backing layer, the cyanoacrylate adhesive spaced away from the fluidic connector; and
        an absorbent layer configured to be positioned between the backing layer and the wound site, the absorbent layer comprising a hydrophobic residue positioned directly beneath the cyanoacrylate adhesive, the hydrophobic residue configured to prevent fluid passage and formed by gaseous material migration from the cyanoacrylate adhesive through the backing layer; and
        wherein the cyanoacrylate adhesive is positioned on the backing layer such that a barrier is created in the absorbent layer, the barrier configured to prevent swelling of the absorbent layer beneath the fluidic connector.

2. The wound treatment apparatus of claim 1, further comprising a wound contact layer beneath the absorbent layer and sealed to the backing layer.

3. The wound treatment apparatus of claim 1, further comprising a source of negative pressure configured to be in fluid communication with the wound site through the wound dressing.

4. The wound treatment apparatus of claim 1, wherein the absorbent layer comprises a vertical hole positioned below the opening in the backing layer.

5. The wound treatment apparatus of claim 1, wherein the cyanoacrylate adhesive is positioned on the backing layer over the entire periphery of the absorbent layer.

6. The wound treatment apparatus of claim 1, wherein the cyanoacrylate adhesive is positioned on the backing layer over one edge of the absorbent layer.

7. The wound treatment apparatus of claim 1, wherein the cyanoacrylate adhesive is positioned on the backing layer in a stripe over the width of the absorbent layer.

8. The wound treatment apparatus of claim 1, wherein the cyanoacrylate adhesive is positioned on the backing layer in four stripes over the width of the absorbent layer.

9. The wound treatment apparatus of claim 1, wherein the cyanoacrylate adhesive is positioned on the backing layer in a square pattern around the distal end of the fluidic connector.

10. A wound treatment apparatus for treatment of a wound site, comprising:
    a wound dressing configured to be positioned over a wound site, the wound dressing comprising:
        a backing layer having an upper surface and a lower surface and defining a perimeter configured to be positioned over skin surrounding the wound site, the backing layer including an opening;
        cyanoacrylate adhesive located on an upper surface of the backing layer;
        an absorbent layer configured to be positioned between the backing layer and the wound site, the absorbent layer comprising a hydrophobic residue, the hydrophobic residue configured to prevent fluid passage and formed by gaseous material migration from the cyanoacrylate adhesive through the backing layer; and wherein the cyanoacrylate adhesive is positioned on the backing layer such that channels are created in the underlying absorbent layer, the channels configured to channel wound exudate to the opening.

11. The wound treatment apparatus of claim 10, wherein the cyanoacrylate adhesive is positioned on the backing layer in the shape of a square.

12. The wound treatment apparatus of claim 10, wherein the cyanoacrylate adhesive is positioned on the backing layer in a pattern comprising a plurality of stripes.

13. The wound treatment apparatus of claim 12 wherein the stripes are parallel.

14. The wound treatment apparatus of claim 12, wherein the stripes are curved.

15. A wound treatment apparatus for treatment of a wound site, comprising:
    a wound dressing configured to be positioned over a wound site, the wound dressing comprising:
        a backing layer having an upper surface and a lower surface and defining a perimeter configured to be positioned over skin surrounding the wound site, the backing layer including an opening;
        a fluidic connector, positioned on the upper surface of the backing layer;
        cyanoacrylate adhesive located on an upper surface of the backing layer, the cyanoacrylate adhesive spaced away from the fluidic connector; and
        an absorbent layer configured to be positioned between the backing layer and the wound site, the absorbent layer comprising a hydrophobic residue positioned directly beneath the cyanoacrylate adhesive , the hydrophobic residue configured to prevent fluid passage and formed by gaseous material migration from the cyanoacrylate adhesive through the backing layer; and wherein the cyanoacrylate adhesive is positioned on the backing layer over an edge of the absorbent layer, such that fluid leakage from the absorbent layer is reduced.

16. The wound treatment apparatus of claim 15, wherein the cyanoacrylate adhesive is positioned over two or more edges of the absorbent layer.

\* \* \* \* \*

UNITED STATES PATENT AND TRADEMARK OFFICE
CERTIFICATE OF CORRECTION

| | |
|---|---|
| PATENT NO. | : 11,090,196 B2 |
| APPLICATION NO. | : 16/067530 |
| DATED | : August 17, 2021 |
| INVENTOR(S) | : John Philip Gowans et al. |

It is certified that error appears in the above-identified patent and that said Letters Patent is hereby corrected as shown below:

On the Title Page

On Page 3, Column 2, Item (56), Line 11, under Other Publications, delete "and" and insert --und--.

In the Specification

In Column 1, Lines 7-8, below "APPLICATIONS" delete "CROSS-REFERENCE TO RELATED APPLICATIONS".

In Column 4, Line 15, delete "mmHg," and insert --inHg,--.

In Column 6, Line 38, delete "113" and insert --1B--.

In Column 7, Line 19, delete "While" and insert --while--.

In Column 8, Line 21, delete "(that" and insert --that--.

In Column 12, Line 39, delete "Gore™ m" and insert --Gore™--.

In Column 16, Line 24, delete "angles," and insert --angles--.

In the Claims

In Column 18, Claim 15, Line 63, delete "adhesive ," and insert --adhesive,--.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*